(12) United States Patent
Shim et al.

(10) Patent No.: US 12,387,338 B2
(45) Date of Patent: Aug. 12, 2025

(54) METHOD FOR AUTOMATED TOOTH SEGMENTATION OF THREE DIMENSIONAL SCAN DATA USING DEEP LEARNING AND COMPUTER READABLE MEDIUM HAVING PROGRAM FOR PERFORMING THE METHOD

(71) Applicant: IMAGOWORKS INC., Seoul (KR)

(72) Inventors: Eungjune Shim, Seoul (KR); Jung-Min Hwang, Seoul (KR); Youngjun Kim, Seoul (KR)

(73) Assignee: IMAGOWORKS INC., Seoul (KR)

( * ) Notice: Subject to any disclaimer, the term of this patent is extended or adjusted under 35 U.S.C. 154(b) by 547 days.

(21) Appl. No.: 17/835,390

(22) Filed: Jun. 8, 2022

(65) Prior Publication Data

US 2022/0398738 A1 Dec. 15, 2022

(51) Int. Cl.
| | |
|---|---|
| *G06F 17/00* | (2019.01) |
| *G06T 7/11* | (2017.01) |
| *G06T 7/12* | (2017.01) |
| *G06T 7/66* | (2017.01) |
| *G06V 10/25* | (2022.01) |
| *G06V 10/82* | (2022.01) |

(52) U.S. Cl.
CPC ............. *G06T 7/11* (2017.01); *G06T 7/12* (2017.01); *G06T 7/66* (2017.01); *G06V 10/25* (2022.01); *G06V 10/82* (2022.01); *G06T 2207/10028* (2013.01); *G06T 2207/20084* (2013.01); *G06T 2207/30036* (2013.01); *G06V 2201/03* (2022.01)

(58) Field of Classification Search
CPC .... G06T 7/11; G06T 7/12; G06T 7/66; G06V 10/25; G06V 10/82
See application file for complete search history.

(56) References Cited

U.S. PATENT DOCUMENTS

| | | | |
|---|---|---|---|
| 10,062,198 B2 * | 8/2018 | Bhat | G06T 7/73 |
| 10,856,954 B1 * | 12/2020 | Raslambekov | A61C 19/04 |
| 11,058,514 B2 * | 7/2021 | Chen | A61C 13/0004 |
| 11,568,533 B2 * | 1/2023 | Anssari Moin | G06T 11/008 |
| 11,896,455 B2 * | 2/2024 | Chen | A61C 7/12 |

(Continued)

FOREIGN PATENT DOCUMENTS

| | | |
|---|---|---|
| KR | 20150145950 A | 12/2015 |
| KR | 20200022564 A | 3/2020 |
| WO | 2020161121 A | 8/2020 |

OTHER PUBLICATIONS

European search report issued on Dec. 20, 2022.

(Continued)

*Primary Examiner* — Mohammed H Zuberi
(74) *Attorney, Agent, or Firm* — LEEPI

(57) ABSTRACT

A method of automated tooth segmentation of a three dimensional scan data using a deep learning, includes determining a U-shape of teeth in input scan data and operating a U-shape normalization operation to the input scan data to generate first scan data, operating a teeth and gum normalization operation, in which the first scan data are received and a region of interest (ROI) of the teeth and gum is set based on a landmark formed on the tooth, to generate second scan data, inputting the second scan data to a convolutional neural network to label the teeth and the gum and extracting a boundary between the teeth and the gum using labeled information of the teeth and the gum.

13 Claims, 11 Drawing Sheets

(56) References Cited

U.S. PATENT DOCUMENTS

| | | | |
|---|---|---|---|
| 2013/0308843 A1* | 11/2013 | Tank | G06T 7/12 |
| | | | 382/128 |
| 2016/0134581 A1 | 5/2016 | Chang et al. | |
| 2018/0085201 A1* | 3/2018 | Wu | G16H 70/60 |
| 2018/0168781 A1* | 6/2018 | Kopelman | G16H 30/20 |
| 2018/0235437 A1* | 8/2018 | Ozerov | A61B 5/4552 |
| 2018/0360567 A1* | 12/2018 | Xue | G06T 7/10 |
| 2019/0060042 A1* | 2/2019 | Fisker | A61C 9/0046 |
| 2019/0163965 A1* | 5/2019 | Yoo | G06V 40/176 |
| 2019/0172200 A1* | 6/2019 | Andreiko | G06V 20/64 |
| 2019/0180443 A1* | 6/2019 | Xue | G06T 7/13 |
| 2020/0000553 A1* | 1/2020 | Makarenkova | A61C 7/002 |
| 2020/0000554 A1* | 1/2020 | Makarenkova | G16H 50/50 |
| 2020/0160497 A1* | 5/2020 | Shah | G06T 7/70 |
| 2021/0174543 A1 | 6/2021 | Claessen et al. | |
| 2022/0146408 A1* | 5/2022 | Koudele | G01N 33/54388 |
| 2022/0398868 A1* | 12/2022 | Hosono | G06V 20/46 |

OTHER PUBLICATIONS

Jacques Treil et. al., The human face as a 3D model for cephalometric analysis, Digital radiography and three dimensional imaging, Feb. 26-27, 2005, p. 139-146, V43, Ann Arbor, Michigan.

Sheng-hui Liao et. al., Automatic tooth segmentation of dental mesh based on harmonic fields, BioMed research International, Jan. 6, 2015, V2015, ID187173, Hindawi Publishing Corp.

BrenaInn Woodsend et. al., Automatic recognition of landmarks on digital dental models, Elsevier, Dec. 25, 2020, p. 26.

Xiaojie Xu et. al., 3D tooth segmentation and labeling using deep convolutional neural networks, IEEE transactions on visualization and computer graphics, Jul. 2019, p. 2336-2346, V25, No. 7.

International search report issued on Mar. 10, 2022.

Xiaojie Xu et al., IEEE transactions on visualization and computer graphics, May 22, 2018, vol. 25, No. 7, pp. 2336-2348.

Farhad Ghazvinian Zanjani et al., Neurocomputing, Jan. 27, 2021, vol. 453, pp. 286-298.

* cited by examiner

METHOD FOR AUTOMATED TOOTH SEGMENTATION OF THREE DIMENSIONAL SCAN DATA USING DEEP LEARNING AND COMPUTER READABLE MEDIUM HAVING PROGRAM FOR PERFORMING THE METHOD

PRIORITY STATEMENT

This application claims priority under 35 U.S.C. § 119 to Korean Patent Application No. 10-2021-0077680, filed on Jun. 15, 2021 in the Korean Intellectual Property Office (KIPO) and International Patent Application No. PCT/KR2021/009146 filed on Jul. 15, 2021, the contents of which are herein incorporated by reference in their entireties.

BACKGROUND

1. Technical Field

Embodiments relate to a method of automated tooth segmentation of a three dimensional scan data using a deep learning and a non-transitory computer-readable storage medium having stored thereon program instructions of the method of the automated tooth segmentation. More particularly, embodiments relate to a method of automated tooth segmentation of a three dimensional scan data using a deep learning reducing a time and an effort for tooth segmentation of the scan data and a non-transitory computer-readable storage medium having stored thereon program instructions of the method of the automated tooth segmentation.

2. Description of the Related Art

For diagnosis, analysis, and prosthesis production in dentistry, a technology for tooth segmentation from a patient's three dimensional scan data may be required. In particular, digital orthodontic treatment using an oral scanner is increasing in the dental field. In orthodontics, it is important to predict the arrangement and occlusion of teeth and establish an appropriate plan. For this, the tooth segmentation is essential.

A conventional method for the tooth segmentation is as follows. First, dental scan data is obtained using the oral scanner. Then, an operator manually designates a tooth boundary, and designates a plane to be used for the tooth segmentation using axis information and the tooth boundary, and checks segmented surfaces between the teeth and corrects portions if necessary. This process may be repeatedly performed for all teeth to obtain tooth segmentation data.

As explained above, when the operator manually designates the tooth boundary with eyes through a two dimensional screen for the three dimensional data, an accuracy may be decreased, a high skill and a lot of time may be required for the operator.

SUMMARY

Embodiments provide a method of automated tooth segmentation of a three dimensional scan data using a deep learning, operated automatically to reduce the time and the effort for the tooth segmentation from the scan data and to enhance the accuracy.

Embodiments provide a non-transitory computer-readable storage medium having stored thereon program instructions of the method of the automated tooth segmentation of the three dimensional scan data using the deep learning.

In an example method of automated tooth segmentation of a three dimensional scan data using a deep learning according to the present inventive concept, the method includes determining a U-shape of teeth in input scan data and operating a U-shape normalization operation to the input scan data to generate first scan data, operating a teeth and gum normalization operation, in which the first scan data are received and a region of interest (ROI) of the teeth and gum is set based on a landmark formed on the tooth, to generate second scan data, inputting the second scan data to a convolutional neural network to label the teeth and the gum and extracting a boundary between the teeth and the gum using labeled information of the teeth and the gum.

In an embodiment, the operating the U-shape normalization operation may include a position normalization operation moving a center of gravity of the input scan data to an origin of a predetermined space.

In an embodiment, when a point cloud of the input scan data is X, a number of points in the point cloud is n, the points in the point cloud is p1, p2, ..., pn, coordinates of a k-th point in the point cloud is xk, yk, zk, and the center of gravity of the input scan data is G(X) in the position normalization operation, $$X = \{p_1, p_2, \ldots, p_n\}, \quad p_k = \{x_k, y_k, z_k\}, \quad G(X) = \frac{\sum_{k=1}^n p_k}{n}$$

may be satisfied.

In an embodiment, the operating the U-shape normalization operation may further include a principal axis normalization operation determining a first principal axis, a second principal axis and a third principal axis which are perpendicular to each other by analyzing principal axes formed by the points in the input scan data.

In an embodiment, a longest axis among the first principal axis, the second principal axis and the third principal axis may be determined to a left-and-right direction of the U-shape in the principal axis normalization operation.

In an embodiment, a shortest axis among the first principal axis, the second principal axis and the third principal axis may be determined to an up-and-down direction of the U-shape in the principal axis normalization operation.

In an embodiment, a second longest axis among the first principal axis, the second principal axis and the third principal axis may be determined to a front-and-back direction of the U-shape in the principal axis normalization operation.

In an embodiment, when a point cloud of the input scan data is X, a number of points in the point cloud is n, the points in the point cloud is p1, p2, ..., pn, coordinates of a k-th point in the point cloud is xk, yk, zk, a covariance matrix of the point cloud is $\Sigma$, a matrix whose column vector is an eigenvector of the covariance matrix $\Sigma$ is A, the eigenvectors of the covariance matrix $\Sigma$ are P, Q, R, a matrix in which the diagonal component is an eigenvalue of $\Sigma$ and element values excluding the diagonal component is 0 is $\Lambda$, the eigenvalues of the covariance matrix $\Sigma$ is $\lambda 1, \lambda 2, \lambda 3$, "Lateral" is a left-and-right direction of the U-shape and "Cranial" is an up-and-down direction of the U-shape in the principal axis normalization operation, $$X = \{p_1, p_2, \ldots, p_n\}, \quad p_k = \{x_k, y_k, z_k\}, \quad \Sigma = \mathrm{cov}(X) = \frac{1}{n-1} XX^T,$$

$$\Sigma A = A\Lambda, \quad A = \begin{matrix} P \\ Q \\ R \end{matrix}, \quad \Lambda = \begin{matrix} \lambda_1 & 0 & 0 \\ 0 & \lambda_2 & 0 \\ 0 & 0 & \lambda_3 \end{matrix}$$

may be satisfied.

In an embodiment, the operating the U-shape normalization operation may further include an up-and-down direction normalization operation aligning the input scan data such that the teeth protrude in a predetermined direction among an upward direction and a downward direction using normal vectors of triangles constituting the input scan data.

In an embodiment, in the up-and-down direction normalization operation, when an angle between a mean of the normal vectors of the triangles and a Y axis of the space is equal to or greater than 90 degrees, the input scan data may be rotated 180 degrees based on a plane formed by a X axis of the space and a Z axis of the space.

In an embodiment, when a number of the triangles in the input scan data is n, normal vectors of the triangles are N, a set of the normal vectors of the triangles is "Normals" and the mean of the normal vectors is MeanNormal(Normals) in the up-and-down direction normalization operation, $$\mathrm{Normals} = \{N_1, N_2, \ldots, N_n\}, \quad \mathit{MeanNormal}(\mathrm{Normals}) = \frac{\Sigma_{k=1}^n N_k}{n}$$

may be satisfied.

In an embodiment, the operating the U-shape normalization operation may further include a front-and-back direction normalization operation determining a front direction of the U-shape based on a point density of a first side area of a X axis and a point density of a second side area of the X axis when a left-and-right direction of the U-shape in the input scan data is the X axis, an up-and-down direction of the U-shape in the input scan data is a Y axis and a front-and-back direction of the U-shape in the input scan data is a Z axis.

In an embodiment, the region of interest (ROI) of the teeth and the gum may be set based on a first landmark disposed between two central incisors, a second landmark and a third landmark disposed at outermost points in a left-and-right direction of the teeth.

In an embodiment, when the teeth protrude an upward direction, a base area disposed under a gum area may be removed in the teeth and gum normalization operation.

In an example non-transitory computer-readable storage medium having stored thereon program instructions, the program instructions is executable by at least one hardware processor to receive input CT slices of a CT image including a maxillofacial bone, segment the input CT slices into a mandible and a portion of the maxillofacial bone excluding the mandible using a convolutional neural network structure, the convolutional neural network structure including an encoder including a first operation and a second operation different from the first operation in a same layer and a decoder including a third operation and a fourth operation different from the third operation in a same layer and accumulate 2D segmentation results which are outputs of the convolutional neural network structure to reconstruct a 3D segmentation result.

According to the method of the automated tooth segmentation of the three dimensional scan data using the deep learning, the method is operated automatically using the deep learning so that the time and the effort for the tooth segmentation from the scan data may be reduced and the accuracy of the tooth segmentation may be enhanced.

Using the U-shape normalization operation and the teeth and gum normalization operation, the accuracy of the automated tooth segmentation may be enhanced. The U-shape normalization operation includes the position normalization operation, the principal axis normalization operation, the Y-axis normalization operation and the Z-axis normalization operation so that the accuracy of the automated tooth segmentation may be enhanced.

BRIEF DESCRIPTION OF THE DRAWINGS

The above and other features and advantages of the present inventive concept will become more apparent by describing in detailed embodiments thereof with reference to the accompanying drawings, in which.

DETAILED DESCRIPTION OF THE EMBODIMENTS

Figure 1:
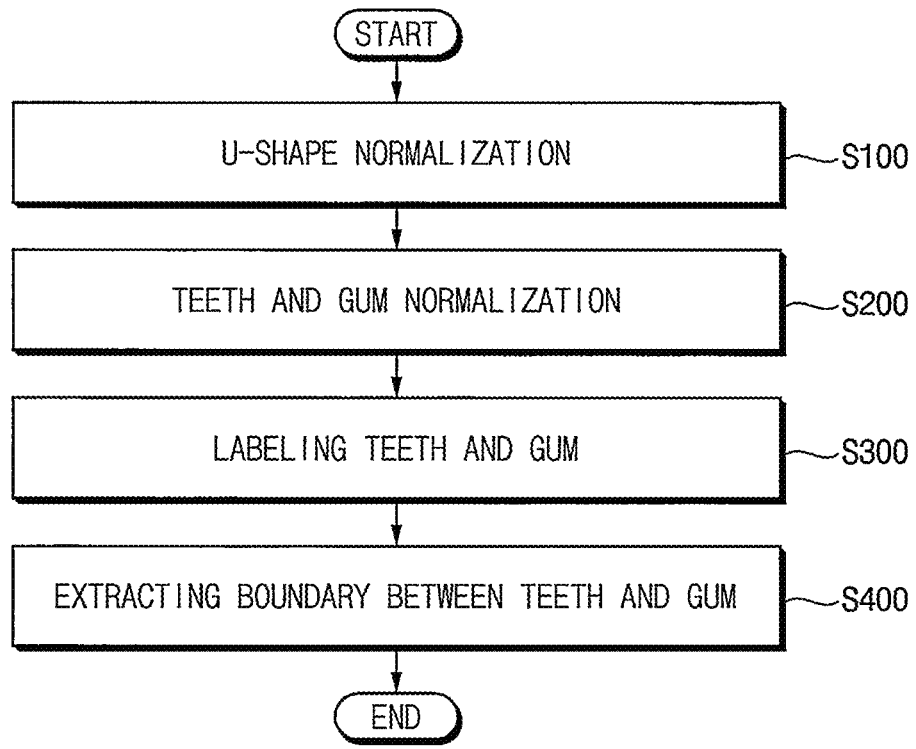
FIG. 1 is a flowchart diagram illustrating a method of automated tooth segmentation of three dimensional scan data according to an embodiment of the present inventive concept.

The present inventive concept now will be described more fully hereinafter with reference to the accompanying drawings, in which exemplary embodiments of the present invention are shown. The present inventive concept may, however, be embodied in many different forms and should not be construed as limited to the exemplary embodiments set fourth herein.

Rather, these exemplary embodiments are provided so that this disclosure will be thorough and complete, and will fully convey the scope of the present invention to those skilled in the art. Like reference numerals refer to like elements throughout.

It will be understood that, although the terms first, second, third, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention.

The terminology used herein is for the purpose of describing particular exemplary embodiments only and is not intended to be limiting of the present invention. As used herein, the singular forms "a," "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

All methods described herein can be performed in a suitable order unless otherwise indicated herein or otherwise clearly contradicted by context. The use of any and all examples, or exemplary language (e.g., "such as"), is intended merely to better illustrate the invention and does not pose a limitation on the scope of the invention unless otherwise claimed. No language in the specification should be construed as indicating any non-claimed element as essential to the practice of the inventive concept as used herein.

Hereinafter, the present inventive concept will be explained in detail with reference to the accompanying drawings.

Figure 2:
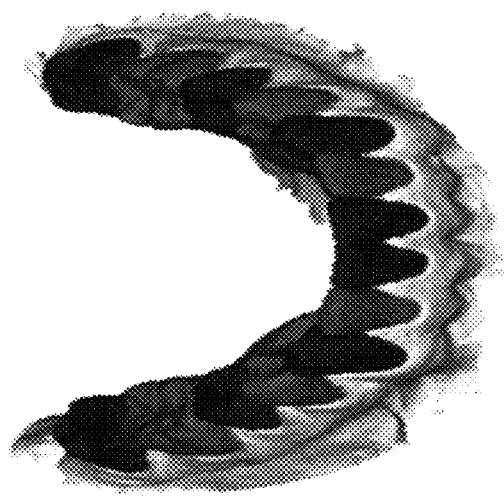
FIG. 2 is a conceptual diagram illustrating a method of automatic point cloud segmentation using graph-based CNN of FIG. 1.

FIG. 1 is a flowchart diagram illustrating a method of automated tooth segmentation of three dimensional scan data according to an embodiment of the present inventive concept. FIG. 2 is a conceptual diagram illustrating a method of automatic point cloud segmentation using graph-based CNN of FIG. 1.

Referring to FIGS. 1 and 2, points of teeth and gum may be automatically labeled in a dental three dimensional scan data using a convolutional neural network (CNN) in the present inventive concept. For example, the convolutional neural network (CNN) may be a graph-based convolutional neural network (CNN).

Generally, a deep learning network structure receives an input value having a fixed size. The three dimensional scan data may be polygon mesh data. The polygon mesh data may include points and edges. The edges may form triangles. Each three dimensional scan data having a type of the polygon mesh data may have different numbers of points, edges and triangles. Thus, when the three dimensional scan data are inputted to the convolutional neural network (CNN), the three dimensional scan data may be extracted in a predetermined size. For example, when the three dimensional scan data are inputted to the convolutional neural network (CNN), the three dimensional scan data may be randomly sampled without replacement in a predetermined size.

For a training of the deep learning, it is necessary to collect a large amount of data and correct answers must be included for all data. In addition, when the data for training and the data for using the trained deep learning model are as normalized as possible, more accurate and precise results may be expected. In the present inventive concept, the U-shape normalization operation (operation S100) and a teeth and gum normalization operation (operation S200) may be used.

The method of the automated tooth segmentation of the three dimensional scan data using the deep learning according to the present embodiment may be operated by a computing apparatus.

In the method of the automated tooth segmentation of the three dimensional scan data using the deep learning according to the present embodiment, a U-shape of teeth may be determined in input scan data, the U-shape normalization operation is operated to the input scan data to generate first scan data (operation S100). The U-shape of the teeth may mean a U-shape of a full arch of the teeth. In dental scan data, position coordinates may not be accurately set, and axes of the data may not be set accurately. The U-shape of the teeth is included somewhere in the input scan data and the position or the direction of the U-shape of the teeth may not be fixed. Thus, when the U-shape normalization operation is not performed, the advantage of the training of the deep learning may be reduced and it is difficult to obtain an accurate tooth segmentation result.

When the input scan data are inputted, a position of the U-shape of the teeth may be displaced to a target position, a principal axis analysis may be operated to match the axes of the input scan data to axes of a predetermined space and the U-shape may be rotated to match the direction of the U-shape to predetermined reference direction if the U-shape is turned upside down or back and forth.

The U-shape normalization operation may be explained referring to FIGS. 3 to 10 in detail.

The teeth and gum normalization operation, in which the first scan data are received and a region of interest (ROI) of the teeth and gum is set based on a landmark formed on the tooth, may be operated to generate second scan data (operation S200). The input scan data may include portions irrelevant to teeth and gum. When the portions irrelevant to the teeth and the gum are also inputted to the convolutional neural network CNN, the accuracy of the tooth segmentation result may be decreased.

After the U-shape normalization operation (operation S100) and the teeth and gum normalization operation (operation S200) are operated to the input scan data, the normalized scan data may be inputted to the convolutional neural network (CNN) as shown in FIG. 2.

The convolutional neural network (CNN) may automatically label the points of the teeth and the gum in the dental three dimensional scan data (operation S300). In FIG. 2, for convenience of explanation, adjacent teeth labeled with different values are shown with different shades.

After the points of the teeth and the gum are labeled, a boundary between the teeth and the gum may be extracted using labeled information of the teeth and the gum (operation S400). For example, when an area of a first tooth is labeled to 1 and an area of a second tooth is labeled to 2, a boundary between points labeled to 1 and points labeled to 2 may be determined to a boundary between the first tooth and the second tooth. In this way, the boundaries between all teeth may be determined and a boundary between the teeth and the gum may be determined.

Figure 3:
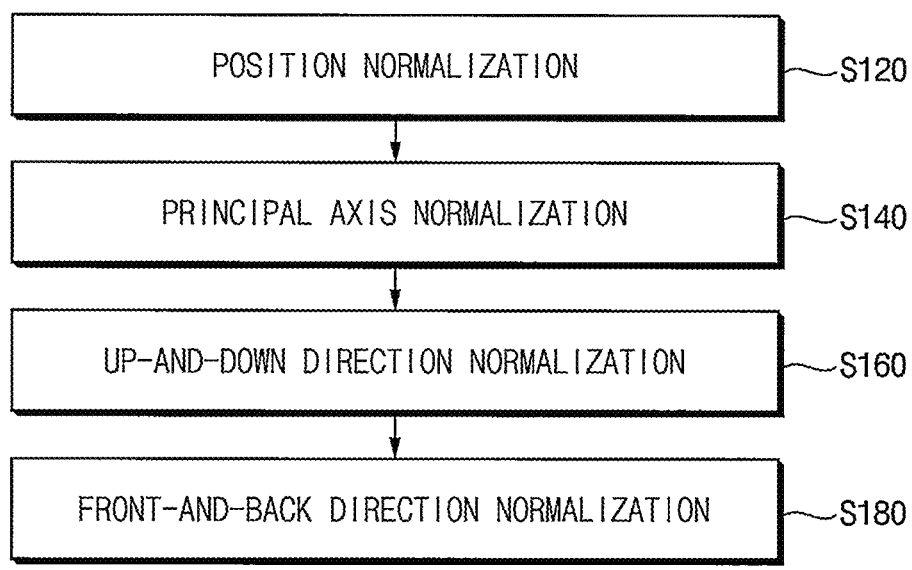
FIG. 3 is a flowchart diagram illustrating a U-shape normalization operation of FIG. 1.
Figure 4:
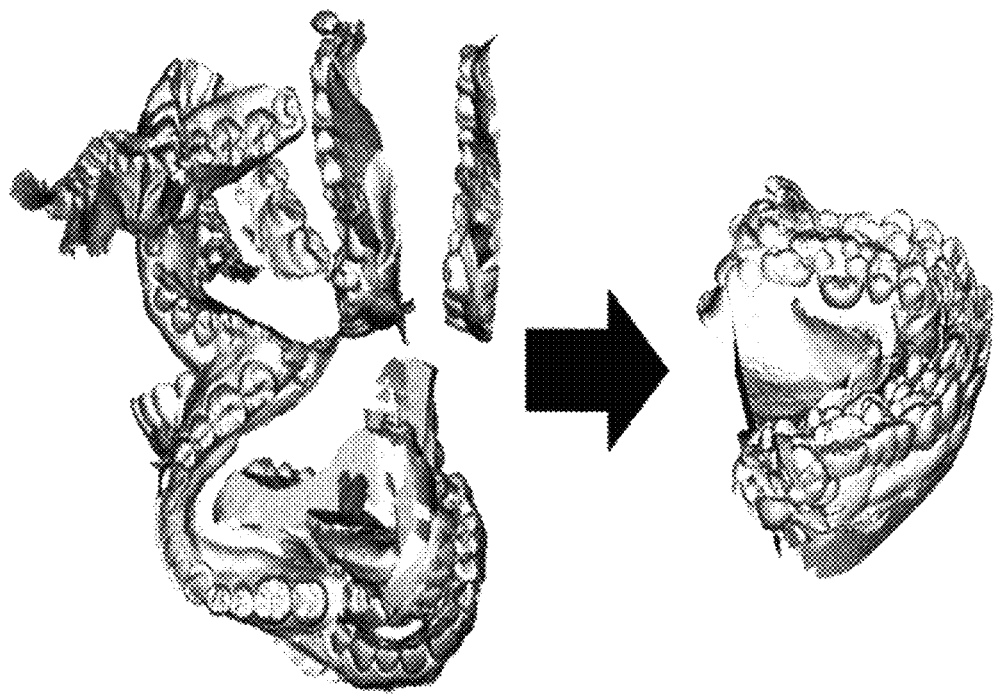
FIG. 4 is a conceptual diagram illustrating the U-shape normalization operation of FIG. 1.

FIG. 3 is a flowchart diagram illustrating the U-shape normalization operation of FIG. 1. FIG. 4 is a conceptual diagram illustrating the U-shape normalization operation of FIG. 1.

Referring to FIGS. 1 to 4, in the U-shape normalization operation, a position normalization operation (operation S120), a principal axis normalization operation (operation S140), an up-and-down direction normalization operation (operation S160) and a front-and-back direction normalization operation (operation S180) may be sequentially operated. However, the present inventive concept may not be limited to a sequence of the normalization operations (operation S120, operation S140, operation S160 and operation S180). For example, unlike FIG. 3, some orders of the normalization operations (operation S120, operation S140, operation S160 and operation S180) may be switched.

A left portion of FIG. 4 represents the input scan data which are not normalized and a right portion of FIG. 4 represents the scan data to which the U-shape normalization operation is applied. When the U-shape normalization operation is completed, the centers of gravity of the scan data coincide with each other, the directions of the three axes of the scan data defining the space coincide with each other, and whether the teeth in the scan data protrude upward or downward coincide with each other, and whether the U-shapes of the teeth in the scan data are convex anteriorly or convex posteriorly coincide with each other.

Figure 5:
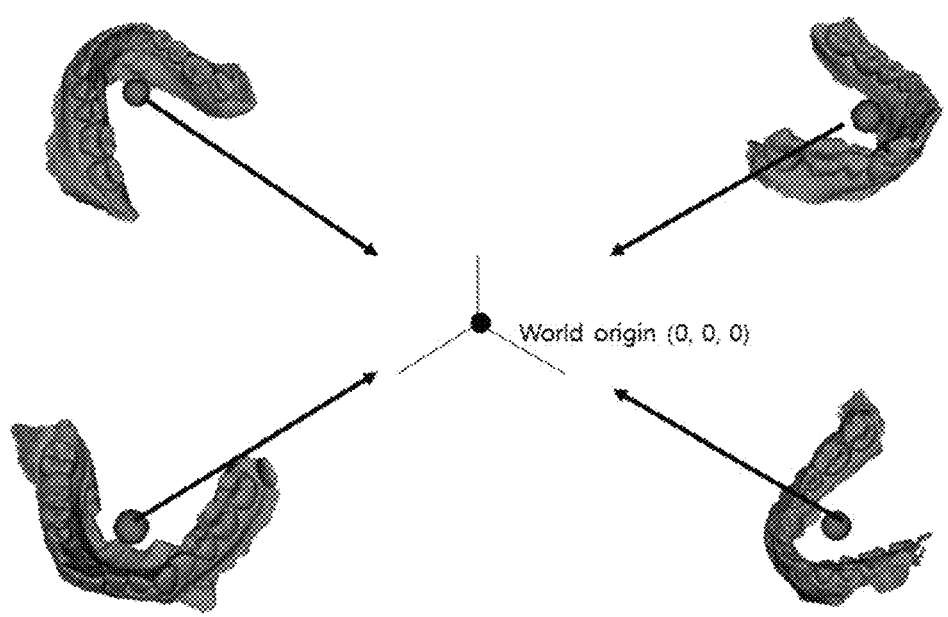
FIG. 5 is a conceptual diagram illustrating a position normalization operation of FIG. 3.
Figure 6:
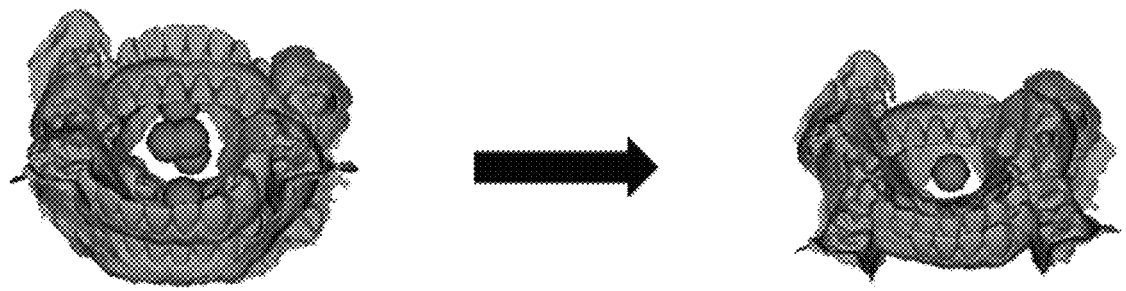
FIG. 6 is a conceptual diagram illustrating a result of the position normalization operation of FIG. 3.

FIG. 5 is a conceptual diagram illustrating the position normalization operation (operation S120) of FIG. 3. FIG. 6 is a conceptual diagram illustrating a result of the position normalization operation (operation S120) of FIG. 3.

Referring to FIGS. 1 to 6, in the position normalization operation (operation S120), the center of gravity of the scan data may be moved to an origin of a predetermined space. The center of gravity of the scan data may be calculated using coordinates of each point in a point cloud forming a mesh.

When the point cloud is X, the number of the points in the point cloud is n, the points in the point cloud is p1, p2, ..., pn, coordinates of a k-th point in the point cloud is xk, yk, zk, and the center of gravity of the input scan data is G(X) in the position normalization operation (operation S120), following Equation 1 may be satisfied.

$$X = \{p_1, p_2, \ldots, p_n\}, \quad p_k = \{x_k, y_k, z_k\}, \quad G(X) = \frac{\sum_{k=1}^{n} p_k}{n} \quad \text{[Equation 1]}$$

As shown in FIG. 5, a difference between the calculated center of gravity and a world origin (0, 0, 0) of the predetermined three dimensional space is calculated and target scan data is moved to the world origin (0, 0, 0) based on the difference.

A left portion of FIG. 6 represents the scan data to which the position normalization operation (operation S120) is not applied and a right portion of FIG. 6 represents the scan data to which the position normalization operation (operation S120) is applied. In the left portion of FIG. 6, the centers of gravity of the scan data, which are indicated by circles, do not coincide with each other. In contrast, in the right portion of FIG. 6, the centers of gravity of the scan data, which are indicated by circles, coincide with each other by the position normalization operation (operation S120).

Figure 7:
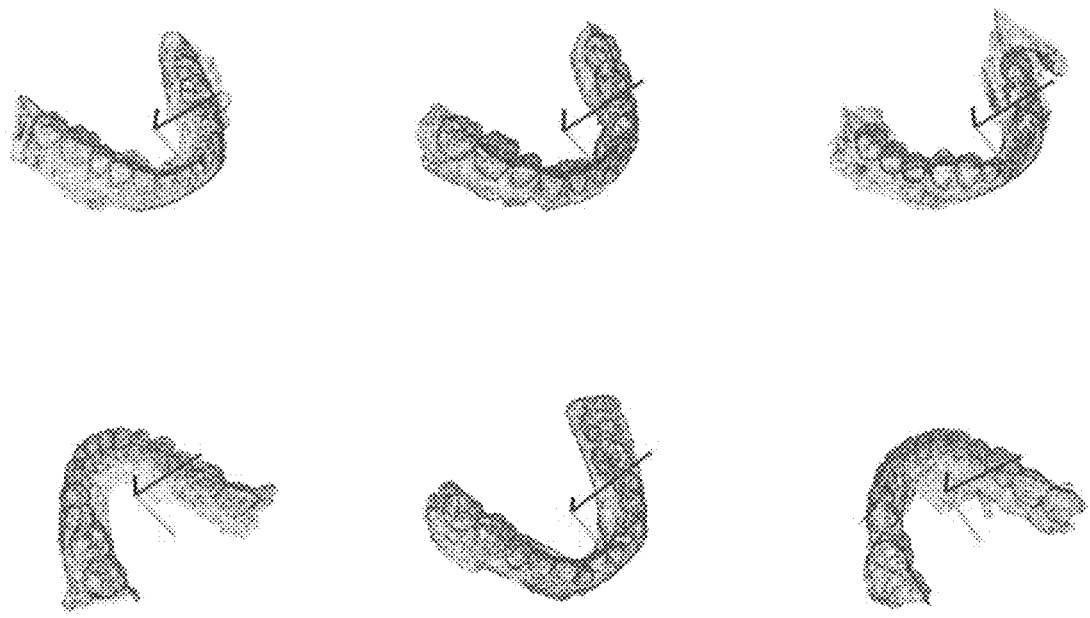
FIG. 7 is a conceptual diagram illustrating a principal axis normalization operation of FIG. 3.
Figure 8A:
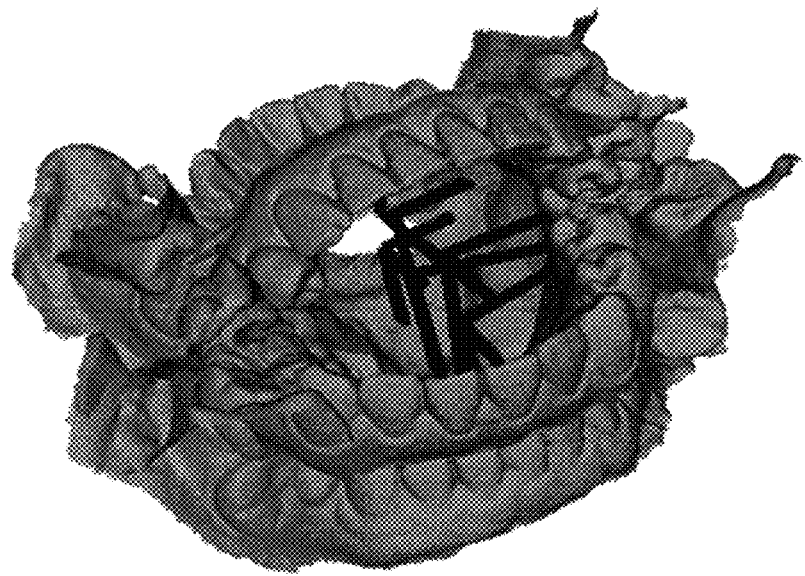
FIGS. 8A, 8B and 8C are conceptual diagrams illustrating a result of the principal axis normalization operation of FIG. 3.
Figure 8B:
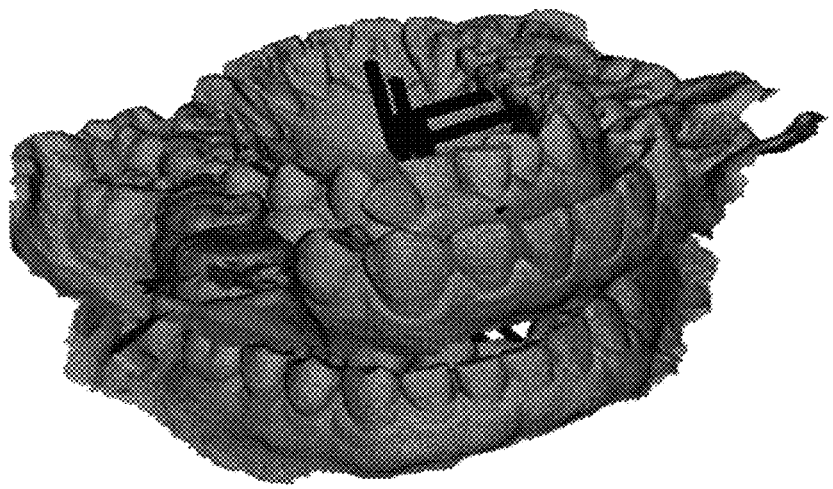
Figure 8C:
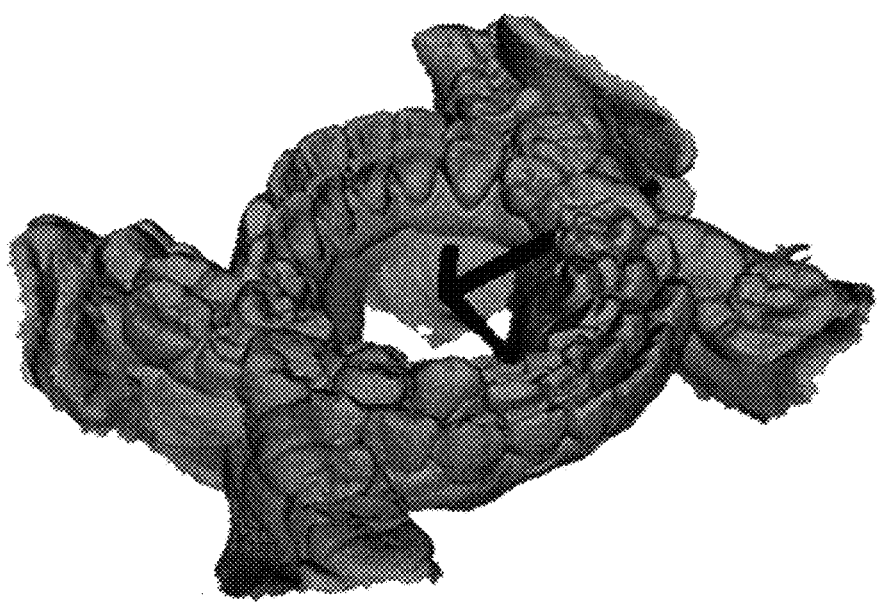

FIG. 7 is a conceptual diagram illustrating the principal axis normalization operation (operation S140) of FIG. 3. FIGS. 8A, 8B and 8C are conceptual diagrams illustrating a result of the principal axis normalization operation (operation S140) of FIG. 3.

Referring to FIGS. 1 to 8C, the principal axis normalization operation (operation S140) may set a spatial orientation through a principal axis analysis. In the principal axis normalization operation (operation S140), a first principal axis, a second principal axis and a third principal axis which are perpendicular to each other may be determined by analyzing the principal axes formed by the points in the scan data.

A longest axis among the first principal axis, the second principal axis and the third principal axis extracted through the principal axis analysis may be determined to a left-and-right direction of the U-shape. A shortest axis among the first principal axis, the second principal axis and the third principal axis may be determined to an up-and-down direction of the U-shape. A second longest axis among the first principal axis, the second principal axis and the third principal axis may be determined to a front-and-back direction of the U-shape.

In FIG. 7, the first principal axes, the second principal axes and the third principal axes of the scan data extracted through the principal axis analysis are illustrated. As shown in FIG. 7, the longest axis among the first principal axis, the second principal axis and the third principal axis may be the left-and-right direction of the U-shape (e.g. X axis), the second longest axis among the first principal axis, the second principal axis and the third principal axis may be the front-and-back direction of the U-shape (e.g. Z axis) and the shortest axis among the first principal axis, the second principal axis and the third principal axis may be the up-and-down direction of the U-shape (e.g. Y axis).

When the point cloud is X, the number of the points in the point cloud is n, the points in the point cloud is p1, p2, ..., pn, coordinates of a k-th point in the point cloud is xk, yk, zk, a covariance matrix of the point cloud is $\Sigma$, a matrix whose column vector is an eigenvector of the covariance matrix $\Sigma$ is A, the eigenvectors of the covariance matrix $\Sigma$ are P, Q, R, a matrix in which the diagonal component is an eigenvalue of $\Sigma$ and element values excluding the diagonal component is 0 is $\Lambda$, the eigenvalues of the covariance matrix $\Sigma$ is $\lambda_1, \lambda_2, \lambda_3$, "Lateral" is the left-and-right direction of the U-shape and "Cranial" is the up-and-down direction of the U-shape in the principal axis normalization operation (operation S140), following Equations 2 to 5 may be satisfied.

$$X = \{p_1, p_2, \ldots, p_n\}, \quad p_k = \{x_k, y_k, z_k\} \quad \text{[Equation 2]}$$

$$\Sigma = \text{cov}(X) = \frac{1}{n-1} X X^T, \quad \Sigma A = A\Lambda \quad \text{[Equation 3]}$$

$$A = \begin{matrix} P \\ Q \\ R \end{matrix}, \quad \Lambda = \begin{matrix} \lambda_1 & 0 & 0 \\ 0 & \lambda_2 & 0 \\ 0 & 0 & \lambda_3 \end{matrix} \quad \text{[Equation 4]}$$

$$\text{Lateral} = A(\text{argmax}([\lambda_1, \lambda_2, \lambda_3])), \quad \text{[Equation 5]}$$

$$\text{Cranial} = A(\text{argmin}([\lambda_1, \lambda_2, \lambda_3]))$$

In FIGS. 8A to 8C, a case in which the principal axis normalization operation (operation S140) is performed prior to the position normalization operation (operation S120) is exemplified.

FIG. 8A represents input scan data to which the normalization operations are not applied at all. FIG. 8B represents the input scan data to which the principal axis normalization operation (operation S140) is applied. In FIG. 8B, the input scan data may be rotated to correspond to the predetermined axial directions. FIG. 8C represents the input scan data to which both the principal axis normalization operation (operation S140) and the position normalization operation (operation S120) are applied. In FIG. 8C, the input scan data may have the same origin and may have the same axes.

Figure 9:
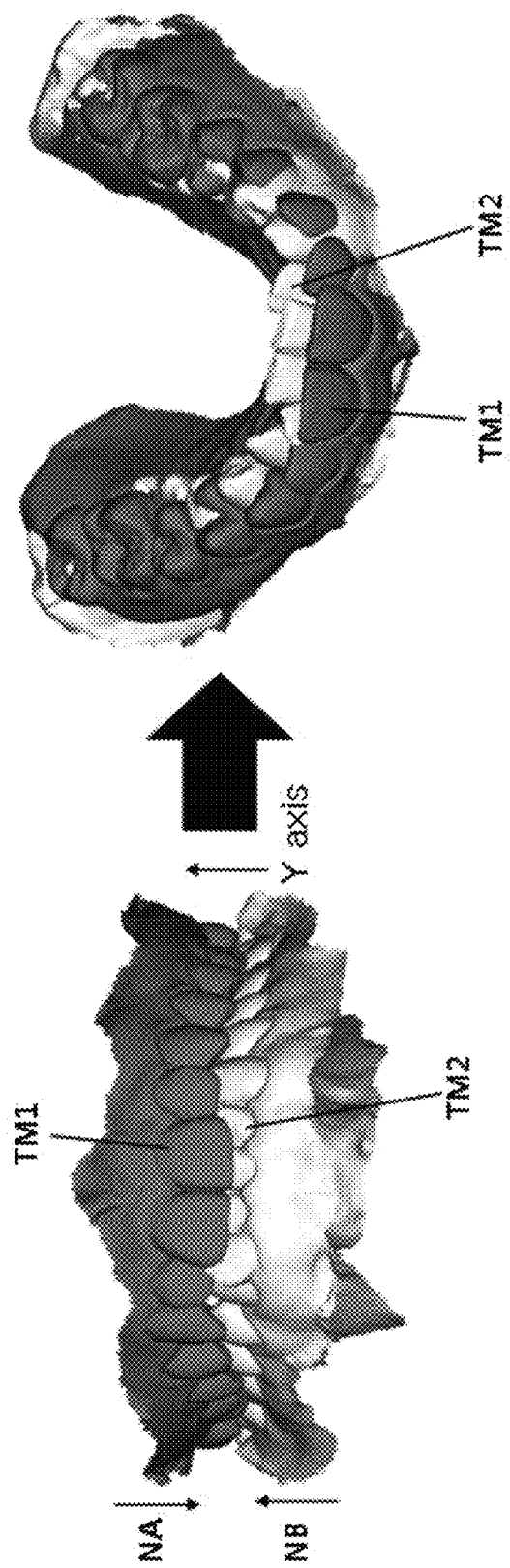
FIG. 9 is a conceptual diagram illustrating an up-and-down direction normalization operation of FIG. 3.

FIG. 9 is a conceptual diagram illustrating the up-and-down direction normalization operation (operation S160) of FIG. 3.

Referring to FIGS. 1 to 9, in the up-and-down direction normalization operation (operation S160), the input scan data may be aligned such that the teeth protrude in a predetermined direction among an upward direction and a downward direction using normal vectors of triangles constituting the input scan data. The up-and-down direction normalization operation may be referred to as a Y-axis normalization operation.

To operation the up-and-down direction normalization operation (operation S160), whether the teeth protrude upward or downward in the input scan data may be determined.

If the predetermined direction is the upward direction and the teeth in the input scan data protrude upward, it is not necessary to rotate the U-shape of the teeth in the input scan data.

In contrast, if the predetermined direction is the upward direction and the teeth in the input scan data protrude downward, the U-shape of the teeth in the input scan data may be rotated 180 degrees based on a plane formed by an X axis of the space and a Z axis of the space.

If the predetermined direction is the downward direction and the teeth in the input scan data protrude downward, it is not necessary to rotate the U-shape of the teeth in the input scan data.

In contrast, if the predetermined direction is the downward direction and the teeth in the input scan data protrude upward, the U-shape of the teeth in the input scan data may be rotated 180 degrees based on the plane formed by the X axis of the space and the Z axis of the space.

When an angle between a mean of the normal vectors of the triangles and the Y axis of the space is equal to or greater than 90 degrees, the input scan data may be rotated 180 degrees based on the plane formed by the X axis of the space and the Z axis of the space. When the angle between the mean of the normal vectors of the triangles and the Y axis of the space is less than 90 degrees, the input scan data may not be rotated.

When the number of the triangles in the input scan data is n, normal vectors of the triangles are N, a set of the normal vectors of the triangles is "Normals" and the mean of the normal vectors is MeanNormal(Normals) in the up-and-down direction normalization operation (operation S160), following Equation 6 may be satisfied.

$$\text{Normals} = \{N_1, N_2, \ldots, N_n\}, \quad \text{[Equation 6]}$$
$$\text{MeanNormal(Normals)} = \frac{\sum_{k=1}^{n} N_k}{n}$$

In FIG. 9, the predetermined direction may be an upward direction. A left portion of FIG. 9 represents two scan data to which the up- and down normalization operation (operation S160) is not applied and a right portion of FIG. 9 represents two scan data to which the up- and down normalization operation (operation S160) is applied.

For first scan data TM1 in the left portion of FIG. 9, a direction of the normal vectors of the triangles may be determined to a direction NA in which the teeth protrude downward. Thus, the U-shape of the teeth in the first scan data TM1 may be rotated 180 degrees.

For second scan data TM2 in the left portion of FIG. 9, a direction of the normal vectors of the triangles may be determined to a direction NB in which the teeth protrude upward. Thus, the U-shape of the teeth in the second scan data TM2 may not be rotated.

The right portion of FIG. 9 represents scan data after the up- and down normalization operation (operation S160), the first scan data TM1 and the second scan data TM2 may have the same Y axis direction in the right portion of FIG. 9.

Figure 10:
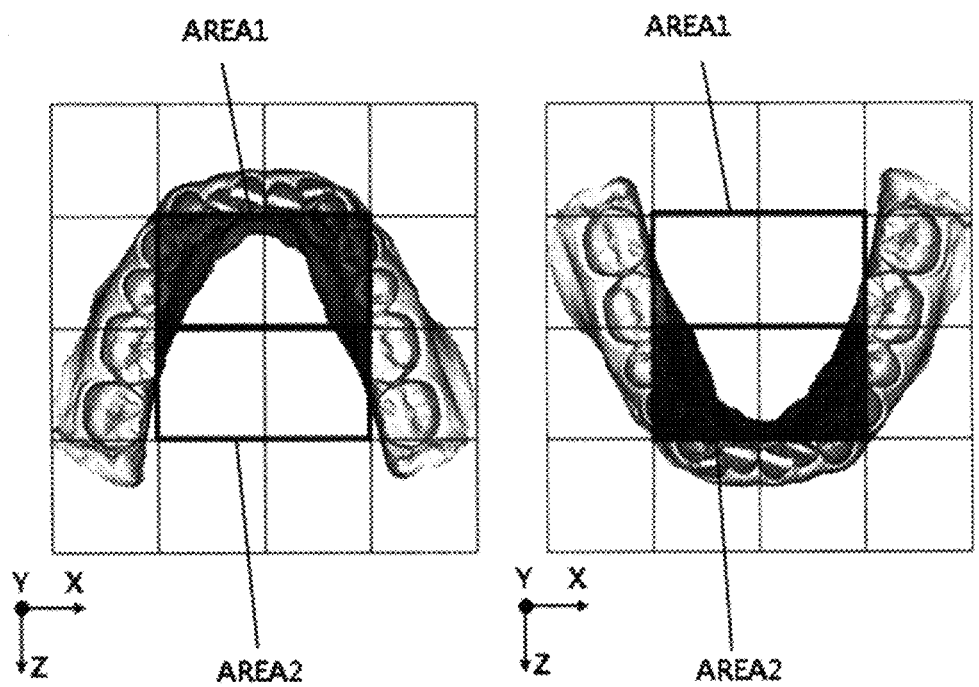
FIG. 10 is a conceptual diagram illustrating a front-and-back direction normalization operation of FIG. 3.

FIG. 10 is a conceptual diagram illustrating a front-and-back direction normalization operation (operation S180) of FIG. 3.

Referring to FIGS. 1 to 10, in the front-and-back direction normalization operation (operation S180), the input scan data may be aligned such that the U-shape of the teeth protrudes in a predetermined direction among an anteriorly convex direction or a posteriorly convex direction. The front-and-back direction normalization operation may be referred to as a Z-axis normalization operation.

The front-and-back direction normalization operation (operation S180) may be operated using a density of the point cloud. In dental scan data, the density of points is generally high around anterior teeth. By analyzing the point distribution, the front-and-back direction normalization operation (operation S180) may be operated.

For example, Octree may be used for the point distribution analysis. The point cloud data X is converted to Octree data structure of leaf 2 and a point density of a first area AREA1 and a point density of a second area AREA2 may be calculated using sixteen nodes. Herein, the first area AREA1 may be assumed as an anterior teeth portion and the second area AREA2 may be assumed as a rear portion.

The first area AREA1 may be a central area of a first side of the X axis and the second area AREA2 may be a central area of a second side of the X axis. The first area AREA1 and the second area AREA2 may have the same width and the same height. When the anterior teeth are disposed in the first area AREA1, the point density of the first area AREA1 may be very high and the point density of the second area AREA2 may be very low since the teeth are rarely disposed in the second area AREA2.

When the point density of the first area AREA1 assumed as the anterior teeth portion is greater than the point density of the second area AREA2 assumed as the rear portion, the scan data may not be rotated. In contrast, when the point density of the second area AREA2 assumed as the rear portion is greater than the point density of the first area AREA1 assumed as the anterior portion, the scan data may be rotated such that the anterior teeth portion and the rear portion are turned over.

When the left-and-right direction of the U-shape in the input scan data is the X axis, the up-and-down direction of the U-shape in the input scan data is the Y axis and the front-and-back direction of the U-shape in the input scan data is the Z axis in the front-and-back direction normalization operation (operation S180), the front direction of the U-shape may be determined based on the point density of a first side area AREA1 of the X axis and the point density of a second side area AREA2 of the X axis.

In a left portion of FIG. 10, the point density of the first area AREA1 assumed as the anterior teeth portion may be greater than the point density of the second area AREA2 assumed as the rear portion so that the scan data may not be rotated.

In a right portion of FIG. 10, the point density of the second area AREA2 assumed as the rear portion may be greater than the point density of the first area AREA1 assumed as the anterior teeth portion so that the scan data may be rotated such that the anterior teeth portion and the rear portion are turned over.

Figure 11:
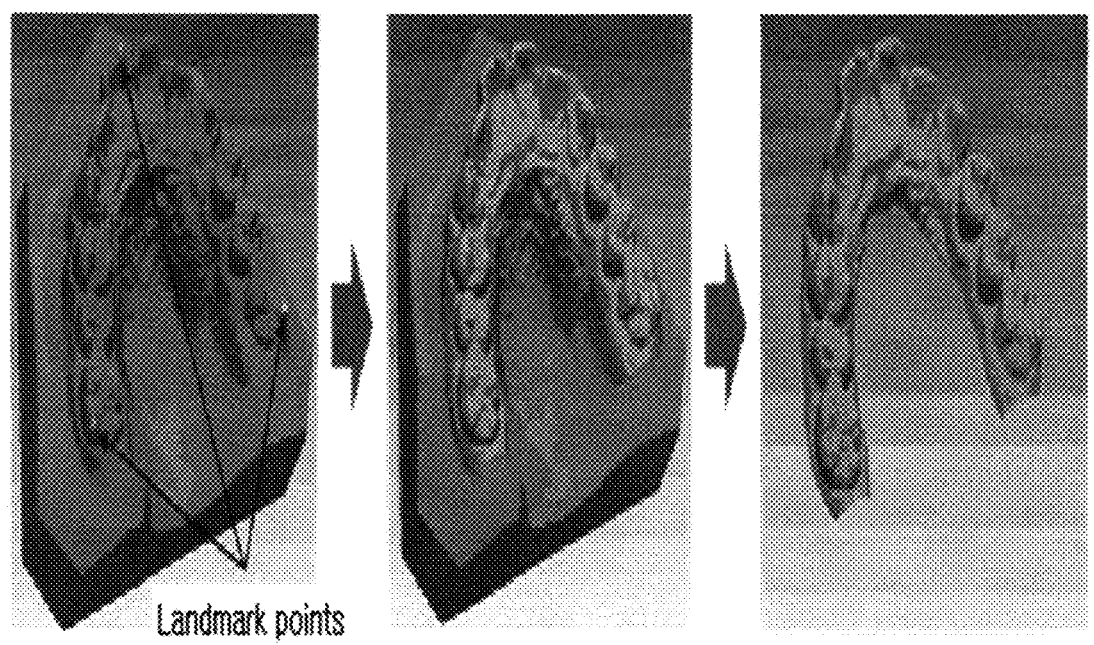
FIGS. 11 and 12 are conceptual diagrams illustrating a teeth and gum normalization operation of FIG. 1.
Figure 12:
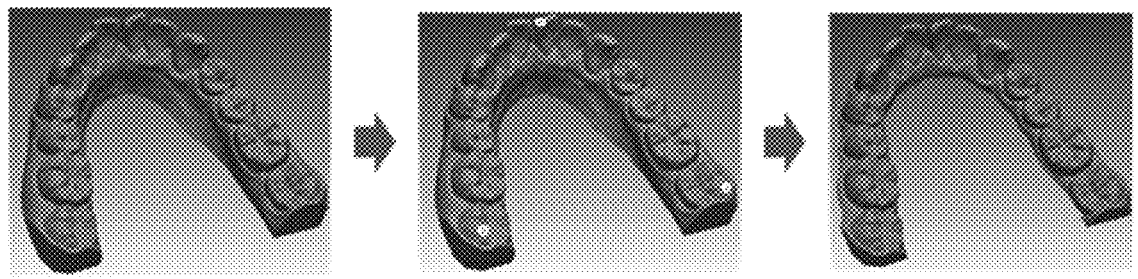

FIGS. 11 and 12 are conceptual diagrams illustrating the teeth and gum normalization operation (operation S200) of FIG. 1.

Referring to FIGS. 1 to 12, in the teeth and gum normalization operation (operation S200), the scan data are received and a region of interest (ROI) of the teeth and the gum may be set based on landmarks disposed on the teeth.

The teeth and gum normalization operation (operation S200) is a method for advanced deep learning inference by extracting the ROI corresponding to the teeth and the gum area of plural scan data.

For example, the teeth and gum normalization operation (operation S200) may be operated using a first landmark disposed between two central incisors, a second landmark and a third landmark disposed at the outermost points in the left-and-right direction of the teeth.

For example, a predetermined distance in front and back of the first landmark may be set as the ROI, a predetermined distance to the left and right of the second landmark may be set as the ROI and a predetermined distance to the left and right of the third landmark may be set as the ROI. A predetermined distance upward and downward of the first to third landmarks may be set as the ROI. Although the ROI is set using three landmarks in the present embodiment, the present inventive concept may not be limited thereto. For example, the number of the landmarks used for setting the ROI may be greater than three.

When the teeth protrude the upward direction, a base area may be disposed under the gum area. The base area is an unnecessary part for the teeth and gum segmentation inference, and the base area may rather adversely affect the teeth and gum segmentation inference. Thus, when the teeth protrude the upward direction, the base area disposed under the gum area may be removed in the teeth and gum normalization operation (operation S200).

The scan data of FIG. 11 may include teeth, a gum and a relatively large base area. The base area disposed under the gum area of FIG. 11 may be removed in the teeth and gum normalization operation (operation S200).

The scan data of FIG. 12 may include teeth, a gum and a relatively small base area. The base area disposed under the gum area of FIG. 12 may be removed in the teeth and gum normalization operation (operation S200).

Figure 13:
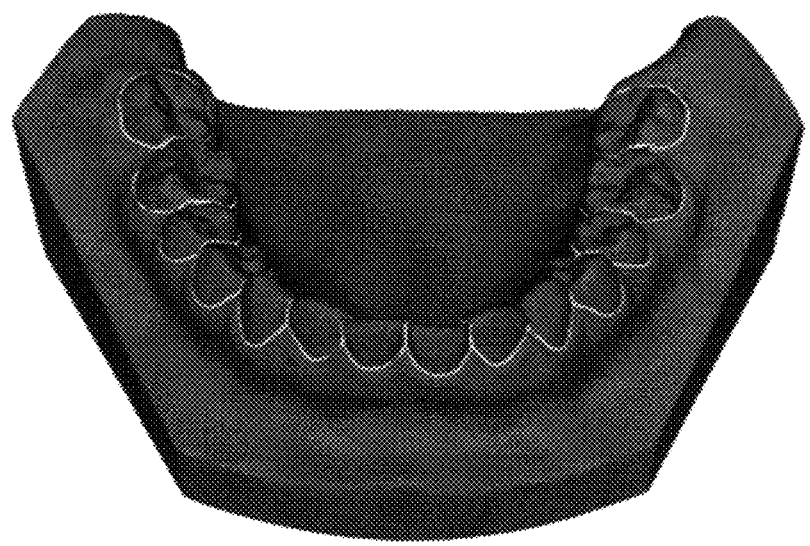
FIGS. 13 and 14 are conceptual diagrams illustrating a boundary extracting operation of FIG. 1.
Figure 14:
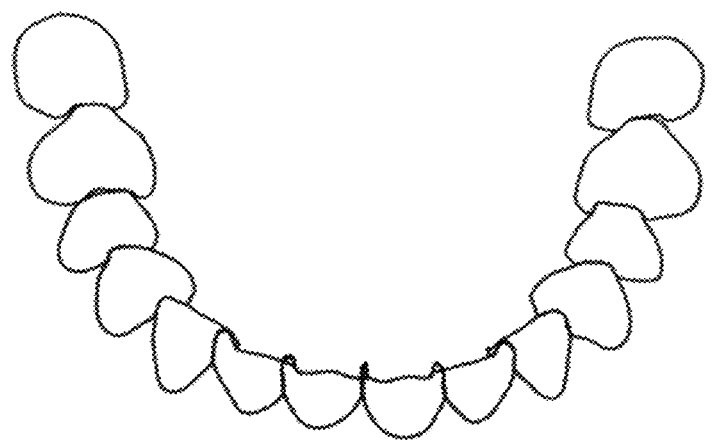

FIGS. 13 and 14 are conceptual diagrams illustrating a boundary extracting operation (operation S400) of FIG. 1.

Referring to FIGS. 1 to 14, after the U-shape normalization operation (operation S100) and the teeth and gum normalization operation (operation S200), the scan data may be inputted to the convolutional neural network so that the teeth and the gum may be labeled (operation S300).

After labeling the teeth and the gum, the boundaries between the teeth and the gum may be extracted based on the labeling information of the teeth and the gum (operation S400). As shown in FIG. 13, a boundary curve connecting boundary areas of the teeth and gum may be generated using the extracted point cloud and polygon mesh information in the boundary extracting operation (operation S400). In FIG. 14, the generated boundary curve is illustrated. Each point constituting the polygon mesh is labeled through the deep learning operation (operation S300) so that the boundary may be easily found based on the labeling result.

According to the present embodiment, the method of automated tooth segmentation of the three dimensional scan data is operated automatically using the deep learning so that the time and the effort for the tooth segmentation from the scan data may be reduced and the accuracy of the tooth segmentation may be enhanced.

Using the U-shape normalization operation (operation S100) and the teeth and gum normalization operation (operation S200), the accuracy of the automated tooth segmentation may be enhanced. The U-shape normalization operation (operation S100) includes the position normalization operation (operation S120), the principal axis normalization operation (operation S140), the Y-axis normalization operation (operation S160) and the Z-axis normalization operation (operation S180) so that the accuracy of the automated tooth segmentation may be enhanced.

According to an embodiment of the present inventive concept, a non-transitory computer-readable storage medium having stored thereon program instructions of the method of the automated tooth segmentation of the three dimensional scan data using the deep learning may be provided. The above mentioned method may be written as a program executed on the computer. The method may be implemented in a general purpose digital computer which operates the program using a computer-readable medium. In addition, the structure of the data used in the above mentioned method may be written on a computer readable medium through various means. The computer readable medium may include program instructions, data files and data structures alone or in combination. The program instructions written on the medium may be specially designed and configured for the present inventive concept, or may be generally known to a person skilled in the computer software field. For example, the computer readable medium may include a magnetic medium such as a hard disk, a floppy disk and a magnetic tape, an optical recording medium such as CD-ROM and DVD, a magneto-optical medium such as floptic disc and a hardware device specially configured to store and execute the program instructions such as ROM, RAM and a flash memory. For example, the program instructions may include a machine language codes produced by a compiler and high-level language codes which may be executed by a computer using an interpreter or the like. The hardware device may be configured to operate as one or more software modules to perform the operations of the present inventive concept.

In addition, the above mentioned method of the automated tooth segmentation of the three dimensional scan data using the deep learning may be implemented in a form of a computer-executed computer program or an application which are stored in a storage method.

The present inventive concept is related to the method of the automated tooth segmentation of the three dimensional scan data using the deep learning and the non-transitory computer-readable storage medium having stored thereon program instructions of the method of the automated tooth segmentation of the three dimensional scan data using the deep learning. According to the present inventive concept, the time and the effort for the tooth segmentation may be reduced and the accuracy of the tooth segmentation may be enhanced.

The foregoing is illustrative of the present inventive concept and is not to be construed as limiting thereof. Although a few embodiments of the present inventive concept have been described, those skilled in the art will readily appreciate that many modifications are possible in the embodiments without materially departing from the novel teachings and advantages of the present inventive concept. Accordingly, all such modifications are intended to be included within the scope of the present inventive concept as defined in the claims. In the claims, means-plus-function clauses are intended to cover the structures described herein as performing the recited function and not only structural equivalents but also equivalent structures. Therefore, it is to be understood that the foregoing is illustrative of the present inventive concept and is not to be construed as limited to the specific embodiments disclosed, and that modifications to the disclosed embodiments, as well as other embodiments, are intended to be included within the scope of the appended claims. The present inventive concept is defined by the following claims, with equivalents of the claims to be included therein.

What is claimed is:

1. A method of automated tooth segmentation of a three dimensional scan data using a deep learning, the method comprising:
   determining a U-shape of teeth in input scan data and operating a U-shape normalization operation to the input scan data to generate first scan data;
   operating a teeth and gum normalization operation, in which the first scan data are received and a region of interest (ROI) of the teeth and gum is set based on a landmark formed on the tooth to generate second scan data;
   inputting the second scan data to a convolutional neural network to label the teeth and the gum;
   extracting a boundary between the teeth and the gum using labeled information of the teeth and the gum;
   wherein the U-shape normalization includes a position normalization to move a center of gravity of the input scan data to an origin of a predetermined space; and,
   wherein when a point cloud of the input scan data is X, a number of points in the point cloud is n, the points in the point cloud is p1, p2, . . . , pn, coordinates of a k-th point in the point cloud is xk, yk, zk, and the center of gravity of the input scan data is G(X) in the position normalization operation, $$X = \{p_1, p_2, \ldots, p_n\}, \quad p_k = \{x_k, y_k, z_k\}, \quad G(X) = \frac{\sum_{k=1}^{n} p_k}{n}$$

are satisfied.

2. The method of claim 1, wherein the operating the U-shape normalization operation further comprises:
   a principal axis normalization operation determining a first principal axis, a second principal axis and a third principal axis which are perpendicular to each other by analyzing principal axes formed by the points in the input scan data.

3. The method of claim 2, wherein a longest axis among the first principal axis, the second principal axis and the third principal axis is determined to a left-and-right direction of the U-shape in the principal axis normalization operation.

4. The method of claim 3, wherein a shortest axis among the first principal axis, the second principal axis and the third principal axis is determined to an up-and-down direction of the U-shape in the principal axis normalization operation.

5. The method of claim 4, wherein a second longest axis among the first principal axis, the second principal axis and the third principal axis is determined to a front-and-back direction of the U-shape in the principal axis normalization operation.

6. The method of claim 2, wherein when a point cloud of the input scan data is X, a number of points in the point cloud is n, the points in the point cloud is p1, p2, . . . , pn, coordinates of a k-th point in the point cloud is xk, yk, zk, a covariance matrix of the point cloud is $\Sigma$, a matrix whose column vector is an eigenvector of the covariance matrix $\Sigma$ is A, the eigenvectors of the covariance matrix $\Sigma$ are P, Q, R, a matrix in which the diagonal component is an eigenvalue of $\Sigma$ and element values excluding the diagonal component is 0 is $\Lambda$, the eigenvalues of the covariance matrix $\Sigma$ is $\lambda_1$, $\lambda_2$, $\lambda_3$, "Lateral" is a left-and-right direction of the U-shape and "Cranial" is an up-and-down direction of the U-shape in the principal axis normalization operation, $$X = \{p_1, p_2, \ldots, p_n\}, \quad p_k = \{x_k, y_k, z_k\}, \quad \Sigma = \text{cov}(X) = \frac{1}{n-1} XX^T,$$

$$\Sigma A = A\Lambda, \quad A = \begin{matrix} P \\ Q \\ R \end{matrix}, \quad \Lambda = \begin{matrix} \lambda_1 & 0 & 0 \\ 0 & \lambda_2 & 0 \\ 0 & 0 & \lambda_3 \end{matrix} \text{ are satisfied.}$$

7. The method of claim 2, wherein the operating the U-shape normalization operation further comprises:
   an up-and-down direction normalization operation aligning the input scan data such that the teeth protrude in a predetermined direction among an upward direction and a downward direction using normal vectors of triangles constituting the input scan data.

8. A method of automated tooth segmentation of a three dimensional scan data using a deep learning, the method comprising:
   determining a U-shape of teeth in input scan data and operating a U-shape normalization operation to the input scan data to generate first scan data;
   operating a teeth and gum normalization operation, in which the first scan data are received and a region of interest (ROI) of the teeth and gum is set based on a landmark formed on the tooth to generate second scan data;
   inputting the second scan data to a convolutional neural network to label the teeth and the gum; and
   extracting a boundary between the teeth and the gum using labeled information of the teeth and the gum,
   wherein the operating the U-shape normalization operation comprises:
   an up-and-down direction normalization operation aligning the input scan data such that the teeth protrude in a predetermined direction among an upward direction and a downward direction using normal vectors of triangles constituting the input scan data, wherein, in the up-and-down direction normalization operation, when an angle between a mean of the normal vectors of the triangles and a Y axis of the space is equal to or greater than 90 degrees, the input scan data are rotated 180 degrees based on a plane formed by a X axis of the space and a Z axis of the space.

9. The method of claim 8, wherein when a number of the triangles in the input scan data is n, normal vectors of the triangles are N, a set of the normal vectors of the triangles is "Normals" and the mean of the normal vectors is Mean-Normal (Normals) in the up-and-down direction normalization operation, $$\text{Normals} = \{N_1, N_2, \ldots, N_n\}, \quad \text{MeanNormal}(\text{Normals}) = \frac{\sum_{k=1}^{n} N_k}{n}$$

are satisfied.

10. The method of claim 7, wherein the operating the U-shape normalization operation further comprises:
a front-and-back direction normalization operation determining a front direction of the U-shape based on a point density of a first side area of a X axis and a point density of a second side area of the X axis when a left-and-right direction of the U-shape in the input scan data is the X axis, an up-and-down direction of the U-shape in the input scan data is a Y axis and a front-and-back direction of the U-shape in the input scan data is a Z axis.

11. The method of claim 1, wherein the region of interest (ROI) of the teeth and the gum is set based on a first landmark disposed between two central incisors, a second landmark and a third landmark disposed at outermost points in a left-and-right direction of the teeth.

12. The method of claim 11, wherein when the teeth protrude an upward direction, a base area disposed under a gum area is removed in the teeth and gum normalization operation.

13. A non-transitory computer readable storage medium having stored thereon program instructions, the program instructions executable by at least one hardware processor to:
determining a U-shape of teeth in input scan data and operating a U-shape normalization operation to the input scan data to generate first scan data;
operating a teeth and gum normalization operation, in which the first scan data are received and a region of interest (ROI) of the teeth and gum is set based on a landmark formed on the tooth, to generate second scan data;
inputting the second scan data to a convolutional neural network to label the teeth and the gum;
extracting a boundary between the teeth and the gum using labeled information of the teeth and the gum;
wherein the U-shape normalization includes a position normalization to move a center of gravity of the input scan data to an origin of a predetermined space; and
wherein when a point cloud of the input scan data is X, a number of points in the point cloud is n, the points in the point cloud is p1, p2, . . . , pn, coordinates of a k-th point in the point cloud is xk, yk, zk, and the center of gravity of the input scan data is G(X) in the position normalization operation, $$X = \{p_1, p_2, \ldots, p_n\}, \quad p_k = \{x_k, y_k, z_k\}, \quad G(X) = \frac{\sum_{k=1}^{n} p_k}{n}$$

are satisfied.

* * * * *